APPLE TREE
Filed Aug. 16 1972 2 Sheets-Sheet 1
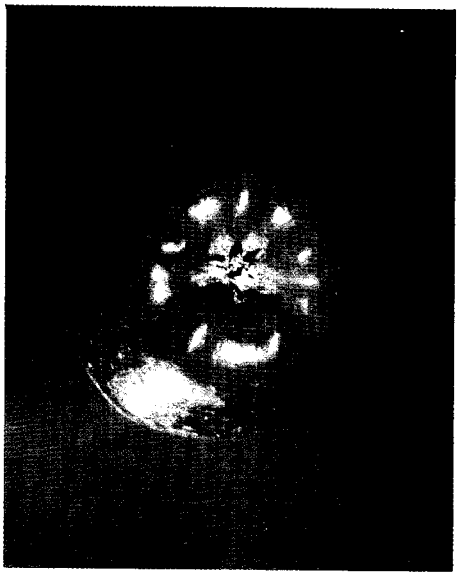
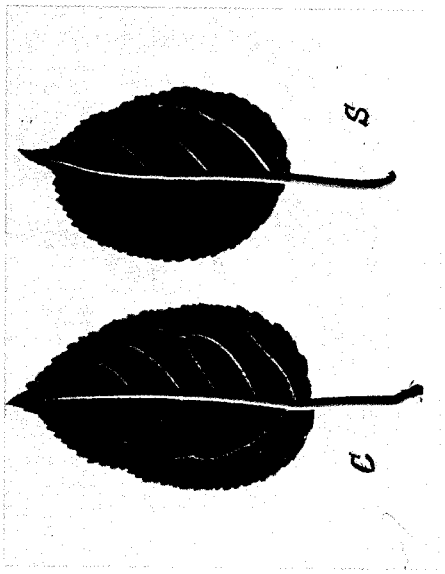
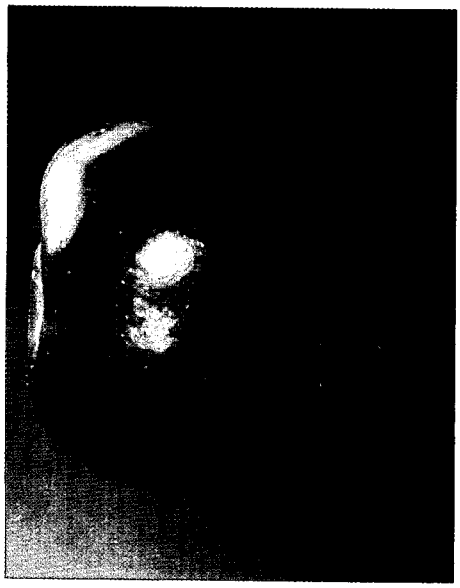
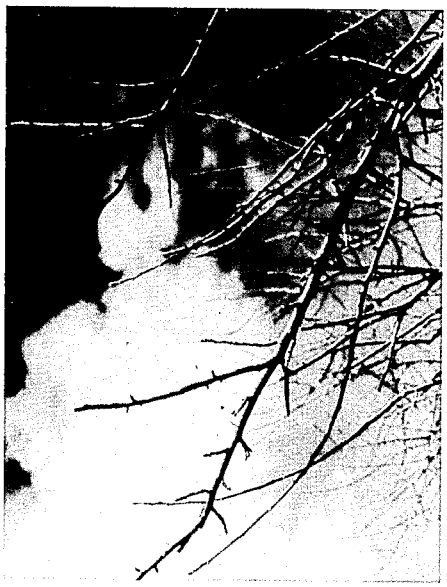

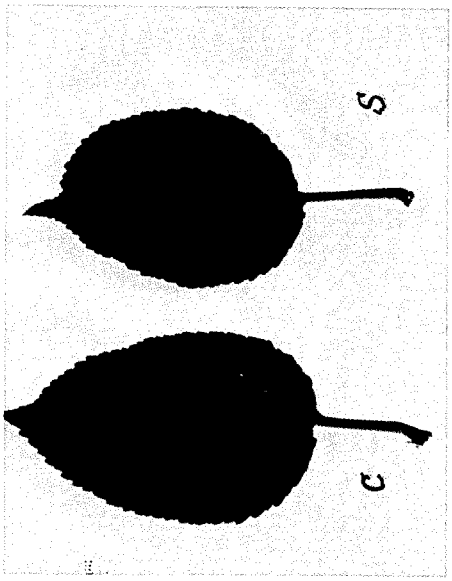
C
S
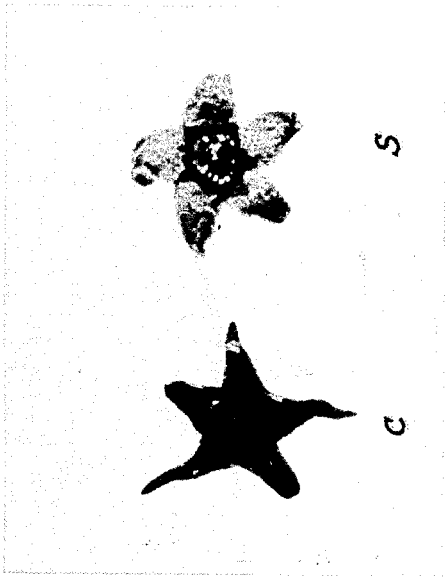
C
S
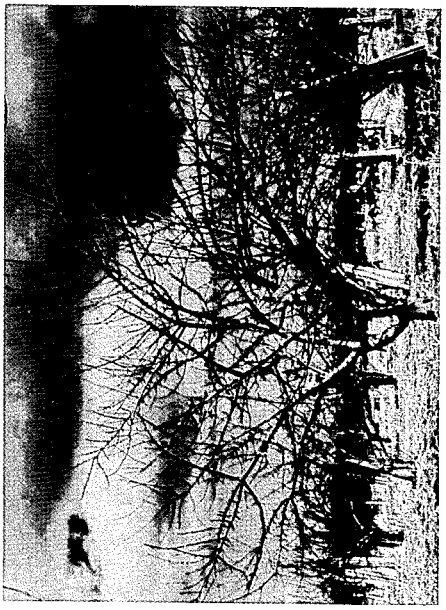
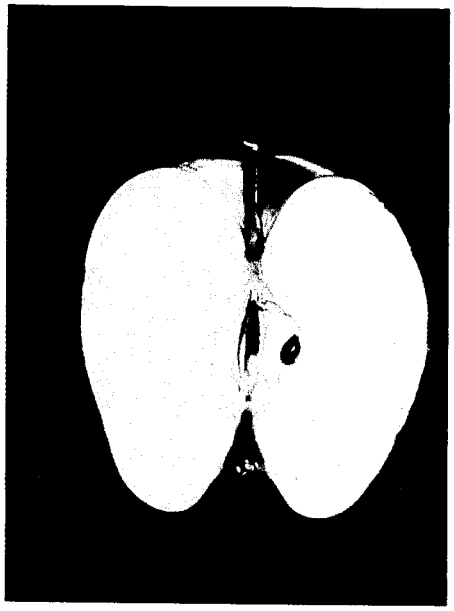

United States Patent Office

Plant Pat. 3,485
Patented Feb. 19, 1974

3,485
APPLE TREE

Stephen M. Coke, Yakima, Wash., assignor to
H. Barry Rose, Alhambra, Calif.

Filed Aug. 16, 1972, Ser. No. 281,113
Int. Cl. A01h 5/03
U.S. Cl. Plt.—35 1 Claim The present invention relates to a new and distinct variety of apple tree which was discovered by me as a whole tree sport of the apple variety commercially known as "Starking Red Delicious" (unpatented), said discovery having been made by me in my cultivated orchard on my property located at Tieton, in Yakima County, Wash.

At the time of my discovery, I was growing in my orchard aforesaid a block of trees of the "Starking Red Delicious" variety aforementioned. During a routine inspection of my orchard, my attention was attracted to one particular tree among the block of "Starking Red Delicious" which bore leaves that were different from those of the other trees in the block, and also bore post bloom fruit having a blood red color on the calyx end thereof, contrary to the usual green color of the small fruit on the trees of "Starking Red delicious." I therefore continue to keep this particular tree under close observation, and in due course, I asexually reproduced the same by grafting, as performed in another of my orchards located at Yakima, Wash.

Continued observations of the original sport tree and the progeny derived therefrom by grafting as aforementioned, including controlled pollen tests conducted on my behalf by professional experts, have convinced me that I have discovered and developed a new and distinct variety of apple tree, as particularly evidenced by the following unique combination of principal characteristics which are outstanding therein and which distinguish it from the variety "Starking Red Delicious" and from all other apple varieties of which I am aware, including all other so-called "Delicious" strains:

(1) A natural semi-dwarf, self-spreading and self-thinning, spur type habit of growth, with the fruit spurs being more numerous per foot of fruiting wood than in any other "Delicious" variety and the fruit spurs beginning to form and set fruit at an unusually early age (usually during the second year), but requiring no thinning by reason of the fact that all but one fruit naturally drops off in all clusters to leave only one fruit per spur;
(2) Heavier leaves of darker green color than in any other "Delicious" apple variety, and the leaves having more prominent feeder veins on their under sides than other varieties;
(3) A regular annual fruit-bearing habit;
(4) A more perfect "Delicious" type fruit form, but the fruit not being as long when mature as the fruit of the variety known as "Starkrimson" Bisbee strain (Plant Pat. No. 1,565);
(5) An unusually early blood red blush of the post bloom fruit on the calyx end, with the little fruit being a solid red color without stripes from the time the fruit sets and remaining a distinctive, attractive and uniform solid dark red color throughout each tree and throughout the fruit growth until the fruit matures;
(6) A superior resistance to lead-arsenic toxicity, particularly in old orchard soils;
(7) Greater frost resistance than most other varieties of the "Delicious" type, and at least as good as Golden varieties;
(8) A self-pollinating habit which is unusual for semi-dwarf red varieties of the "Delicious" type, and also an ability to pollinate the variety "Starking Red Delicious"; and
(9) Good keeping qualities of the fruit in ordinary storage without the need of controlled atmosphere.

The accompanying drawings show a typical tree specimen of my new variety and typical specimens of the fruit, fruit spurs, foliage and the calyx end of a typical small fruit just after setting of the fruit, with the foliage and small fruit specimens being identified as "C" and being shown in comparison with corresponding specimens of "Starking Red Delicious" identified as "S," all as illustrated in color as nearly true as it is reasonably possible to make the same in a color illustration of this character.

The following is a detailed description of my new variety, with color terminology in accordance with the Nickerson Color Fan, published by Munsell Color Company, Inc., of Baltimore, Md., except where general color terms of ordinary dictionary significance are obvious:

Parentage: Sport of "Starking Red Delicious."
Propagation: Holds its distinguishing characteristics through succeeding propagations by grafting.
Locality where grown and observed: Yakima, Wash.
Dates of first and last pickings: About 150 days, and from 155 to 160 days, respectively, after bloom at Yakima, Wash.
Tree: Medium size (semi-dwarf; vigorous; self-spreading (requires no spreaders or manual labor); dense; round-topped; rapid growing; hardy; very productive; regular annual bearer.
*Trunk.*—Medium size; medium smoothness.
*Branches.*—Medium thickness; medium smoothness; much-branched. Color—Moderate Olive Brown, No. 2.5 Y 4/4. Lenticals—Medium number; small.
*Leaves*—Large; wide; long; ovate; abruptly-pointed; thick; smooth. Length—About 3½ inches. Width—About 2¼ inches. Color—Moderate Olive Green, No. 7.5 GY 4/4. Margin—Finely serrate. Petiole—Medium Length (about 1 5/16 inches; medium thickness.
Flowers: Early; medium size.
*Dates of first and full bloom.*—About May 7, and May 10, respectively, at Yakima, Wash.
*Color.*—White.
Fruit:
*Maturity when described.*—Hard-ripe; about Oct. 7 or about 150 days from full bloom, at Yakima, Wash.
*Size.*—Uniform. Axial diameter—About 2 11/16 inches. Transverse diameter—About 3½ inches.
*Form.*—Uniform; symmetrical; regular at base; conical.
*Cavity at stem end.*—Symmetrical; acute toward apex. Depth—About ½ inch. Breadth—About ½ inch. Markings—None.
*Basin at calyx end.*—Symmetrical; narrow; furrowed; crowned.
*Stem.*—Stout. Length—About 1 inch.
*Calyx.*—Closed; segments persistent; narrowly lanceolate; about ½ inch long; imbricate at base; reflexed from base; outer surface glabrous; inner surface pubescent.
*Eye.*—Small; partially closed.
*Skin.*—Thick; smooth; glossy; waxed. Dots—Obscure; many; small; depressed; circular. Color—White; distribution—evenly. Ground color—Dark Red, No. 5 R 3/7. Color markings—Bright, solid dark red blush. Bloom—Abundant. Scarfskin—Light to wanting. General color effect—Solid, bright, Dark Red Blush, No. 5 R 3/7 over entire surface of fruit from time it sets through maturity.

*Flesh.*—Juicy. Color—White. Texture—Hard; fine; crisp. Flavor—Mild; sweet; rich. Aroma—Pronounced. Quality—Best.

*Core.*—Median. Bundle area—Medium size; symmetrical. Halves of core area—Equal. Carpellary area—Star-shaped. Calyx-tube—Apex shouldered. Stem of funnel—short; depth of tube to shoulder—about ½ inch inside. Styles—Distinct. Stamens—In one distinct whorl. Seed cells—Closed. Cell walls—thick; tough; length—about ½ inch; Breadth—about ⅜ inch.

Seeds: Usually 6 and all perfect; usually 2 per cell.

*Length.*—About ¼ inch.

*Breadth.*—About ⅜ inch.

*Form.*—Obtuse.

*Color.*—Moderate Reddish Brown, No. 10 R 3/4.

Use: Market; dessert.

Keeping quality: Good; at least 210 days in ordinary storage (from October through May 15).

Insect and disease resistance: Medium resistance to insects and good resistance to ordinary apple diseases, but superior resistance to lead-arsenic toxicity in soils, as determined by comparison with other apple varieties grown under the same conditions in the region of Yakima, Wash.; easier to propagate and grow than Goldens, Jons, Romes or Saps.

I claim:

1. A new and distinct variety of apple tree, substantially as herein shown and described, characterized particularly as to novelty by the unique combination of a natural semi-dwarf, self-spreading and self-thinning, spur type habit of growth, with the fruit spurs being more numerous per foot of fruiting wood than in any other "Delicious" variety and the fruit spurs beginning to form and set fruit at an unusually early age (usually during the second year), but requiring no thinning by reason of the fact that all but one fruit naturally drops off in all clusters to leave only one fruit per spur, heavier leaves of darker green color than in any other "Delicious" apple variety, and the leaves having more prominent feeder veins on their under sides than other varieties, a regular annular fruit-bearing habit, a more perfect "Delicious" type fruit form, but the fruit not being as long when mature as the fruit of the variety known as "Starkrimson" Bisbee strain (Plant Pat. No. 1,565), an unusually early blood red blush of the post bloom fruit on the calyx end, with the little fruit being a solid red color without stripes from the time the fruit sets and remaining a distinctive, attractive and uniform solid dark red color throughout each tree and throughout the fruit growth until the fruit matures, a superior resistance to lead-arsenic toxicity, particularly in old orchard soils, greater frost resistance than most other varieties of the "Delicious" type, and at least as good as Golden varieties, a self-pollinating habit which is unusual for semi-dwarf red varieties of the "Delicious" type, and also an ability to pollinate the variety "Starking Red Delicious," and good keeping qualities of the fruit in ordinary storage without the need of controlled atmosphere.

No references cited.

ROBERT H. BAGWILL, Primary Examiner